United States Patent [19]

Mitchell et al.

[11] Patent Number: 5,462,946
[45] Date of Patent: Oct. 31, 1995

[54] NITROXIDES AS PROTECTORS AGAINST OXIDATIVE STRESS

[75] Inventors: James B. Mitchell, Damascus, Md.; Amram Samuni, Jerusalem, Islamic Rep. of Iran; William DeGraff, Wheaton, Md.; Stephen Hahn, Great Falls, Va.

[73] Assignee: The United States of America as represented by the Department of Health and Human Services, Washington, D.C.

[21] Appl. No.: 859,622

[22] Filed: Mar. 20, 1992

Related U.S. Application Data

[63] Continuation of Ser. No. 494,532, Mar. 16, 1990, abandoned.

[51] Int. Cl.$^6$ ............ A61K 31/445; A61K 31/505; A61K 31/52; A61K 31/44; A61K 31/425; A61K 31/415; A61K 31/40

[52] U.S. Cl. ............ 514/315; 514/256; 514/261; 514/352; 514/370; 514/377; 514/398; 514/406; 514/426; 514/427

[58] Field of Search ............ 514/315, 427, 514/398, 377, 370, 406, 426, 352, 256, 261

[56] References Cited

FOREIGN PATENT DOCUMENTS

| 8805044 | 7/1988 | WIPO . |
|---|---|---|
| 8805653 | 8/1988 | WIPO . |

OTHER PUBLICATIONS

*Chemical Abstracts* 113(7):57–854n, 1989, Rao et al. Influence of dietary riboflavin deficiency on lenticular glutathione redox cycle, lipid peroxidation, & free radical scavengers in the rat.

*Chemical Abstracts* 110(22):201931t, 1988, Chen et al. Florescence quenchihg of LUEUQH–type complexes by stable free radical.

E. G. Rozantsev (1970) Free Nitroxyl Radicals, Plenum Press, New York, pp. 212–216.

Chemical Abstracts (1967) vol. 66, No. 4, p. 1626, Abstract No. 16925d.

Chemical Abstracts (1991) vol. 115, No. 9, p. 379, Abstract No88347v.

Kristl et al. (1989) Drug Dev. and Industrial Pharmacy, 15(9):1423–1440.

Nilsson et al, The Journal of Biological Chemistry, vol. 264, No. 19, pp. 11131–11135 (Jul. 5, 1989).

Fridovich (1979) Oxygen Free Radicals and Tissue Damage, Ciba Foundation Symposium 65, pp. v–vi and 1–4.

Weiss et al. eds. (1988) Perspectives in Radioprotection, Pharmacology and Therapeutics 39:1–407 (Table of Contents Only).

Mitchell et al. (1987) Br. J. Cancer 55, Suppl. VIII, 96–104.

Grant et al. (1987) Grant & Hackh's Chemical Dictionary, Fifth Ed., McGraw–Hill Book Company, New York, p. 487.

Carey et al. (1977) Advanced Organic Chemistry, Part A: Structure and Mechahisms, Plenum Press, New York, pp. 467–468.

DeGraff et al. (1991) Antimutagenicity of a Low Molecular Weight Superoxide Dismutase Mimic Against Oxidative Mutagens, accepted for publication.

Gelvan et al. (1990) Free Radical Biology and Medicine, vol. 9, Suppl. 1, p. 153, Abstract 16.11.

Reddan et al. (1990) Free Radical Biology and Medicine, vol. 9, Suppl. 1, p. 20, Abstract 2.46.

Fridovich, Archives of Biochemistry and Biophysics, vol. 247, No. 1, pp. 1–11, 1986.

McCord, The New England Journal of Medicine, vol. 312, No. 3, pp. 159–163, 1985.

Samuni et al., Free Radical Biology & Medicine, vol. 6, pp. 141–148, 1989.

Samuni et al., The Journal of Biological Chemistry, vol. 263, No. 34, pp. 17921–17924, 1988.

Weiss, Acta Physiol Scand, Suppl. 548, pp. 9–37, 1986.

*Primary Examiner*—Raymond Henley, III
*Assistant Examiner*—William R. A. Jarvis
*Attorney, Agent, or Firm*—Birch, Stewart, Kolasch & Birch

[57] ABSTRACT

The instant invention is directed to the use of a biologically compatible composition, containing an effective amount of a metal independent nitroxide compound which is preferably represented by the formula

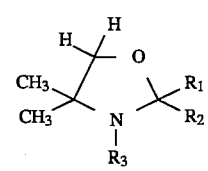

wherein $R_1$ is $-CH_3$; $R_2$ is $-C_2H_5$, $-C_3H_7$, $-C_4H_9$, $-C_5H_{11}$, $-C_6H_{13}$, $-CH_2-CH(CH_3)_2$, $-CHCH_3C_2H_5$, or $-(CH_2)_7-CH_3$, or wherein $R_1$ and $R_2$ together form spirocyclopentane, spirocyclohexane, spirocycloheptane, spirocyclooctane, 5-cholestane, or norbornane, $R_3$ is $-O$. or $-OH$, or a physiologically acceptable salt thereof, and a pharmaceutically acceptable carrier, as antioxidants capable of protecting cells, tissues, organs, and whole organisms against the deleterious effects of harmful oxygen-derived species generated during oxidative stress.

34 Claims, 9 Drawing Sheets

NITROXIDES AS PROTECTORS AGAINST OXIDATIVE STRESS

This application is a continuation of application Ser. No. 07/494,532 filed on Mar. 16, 1990, now abandoned.

BACKGROUND OF THE INVENTION

1. Field of the Invention

The present invention relates to pharmaceutical compositions containing nitroxide compounds useful in ameliorating the deleterious effects of toxic oxygen-related species in living organisms, and methods of using the same.

2. Description of Related Art

The utilization of oxygen by mammals carries both a blessing and a potential curse. The blessing is that all mammals require oxygen for life. The potential curse is that during the metabolism of oxygen, a variety of toxic oxygen-related species such as hydroxyl radical, (.OH); hydrogen peroxide, ($H_2O_2$); and superoxide, ($O_2^-$) are produced. Left unchecked, these free radical species could undoubtedly damage cells. However, cells have evolved elaborate detoxification and repair systems to rid themselves of these potentially toxic and undesirable metabolic by-products: superoxide dismutase (SOD) can convert superoxide to $H_2O_2$, and catalase (CAT) can convert $H_2O_2$ to $H_2O$.

Yet another means to detoxify $H_2O_2$ (and organoperoxides) is via the enzyme glutathione peroxidase (GPX), which with glutathione (GSH), also converts $H_2O_2$ to $H_2O$. Glutathione transferase (GST), in addition to its ability to conjugate and inactivate drugs and xenobiotics, also possesses peroxidase activity and can detoxify $H_2O_2$. These systems represent the major detoxification pathways for oxygen-derived free radicals species; however, there are doubtless other systems that may provide protection including protein sulfhydryls and other thiol-related enzymes that could be involved in repair mechanisms.

Despite the efficiency of these enzymatic systems, there is a small "leakage" of toxic species beyond the biochemical defense network. Of particular importance is the ultimate fate of $H_2O_2$ should it escape detoxification. $H_2O_2$, itself an oxidant capable of damaging biologically important molecules, can also undergo reduction via ferrous complexes to produce .OH. This reaction (often referred to as Fenton chemistry) produces the highly reactive .OH, which in the order of $10^{-9}$ seconds, can: 1) abstract electrons from organic molecules; 2) break chemical bonds; 3) initiate lipid peroxidation; and 4) react with another .OH to produce $H_2O_2$. It is not known whether chronic exposure to low level oxygen-derived free radical species is deleterious; however, it is postulated that the process of aging may be a manifestation of the organisms's inability to cope with sustained oxidative stress. Many modalities used in cancer treatment including x-rays and some chemotherapeutic drugs exert their cytotoxicity via production of oxygen-related free radicals, thereby imposing an added burden to normal detoxification systems. Additionally, free radicals and toxic oxygen-related species have been implicated in ischemia/reperfusion injury, and have long been thought to be important in neutrophil-mediated toxicity of foreign pathogens. Likewise, free radical damage has been implicated in carcinogenesis. The term "oxidative stress" has thus emerged to encompass a broad variety of stresses, some of which have obvious implications for health care.

There has been considerable interest in devising additional approaches, apart from inherent intracellular detoxification systems, to protect cells, tissues, animals, and humans from the toxic effects of any agent or process that imposes oxidative stress. In the past few years, experimental studies have indicated that enzymes such as catalase and superoxide dismutase, and agents such as allopurinol and metal chelating compounds, afford protection against oxidative stress. None of these approaches is at present being applied to humans.

The application of the nitroxides of the instant invention is novel in this respect, and affords several unique advantages. Although the group of chemical compounds called stable nitroxide spin labels has had extensive biophysical use, they have never been used as antioxidants. They exhibit low reactivity with oxygen itself. Being low molecular weight, uncharged, and soluble in aqueous solution, they readily cross into the intracellular milieu. Enzymes such as catalase and superoxide dismutase do not. Therefore, the nitroxides should be superior to catalase and superoxide dismutase in that they can exert protection inside the cell. They are active within the biological pH range of about 5 to 8. Nitroxides are not proteins; therefore, the possibility of antigenic stimulation is remote. Previous low molecular weight superoxide dismutase mimics have all been metal dependent. The current agents do not contain metals, and problems with dissociation constants and deleterious metal induced reactions are therefore avoided. These compounds are apparently non-toxic at effective concentrations, and their lipophilicity can be controlled by the addition of various organic substituents, facilitating targeting of the molecules to specific organs or organelles where toxic oxygen-derived species are generated, to regions which are particularly susceptible to oxidative damage, or to the brain, if this is so desired. Previous radiation protectors have been sulfhydryl-group dependent. The current agents do not have a sulfhydryl group. Finally, previous use of these types of compounds as magnetic resonance contrast agents does not relate to their instant application as antioxidants.

SUMMARY OF THE INVENTION

Accordingly, it is an object of the present invention to overcome the problems associated with the use of impermeable enzymatic detoxifying agents such as superoxide dismutase and catalase to protect living tissues from the deleterious effects of toxic products generated during oxygen metabolism. This is accomplished by providing a pharmaceutical composition containing the nitroxide compounds by any means, and methods for using the same as metal independent, low molecular weight antioxidant for use as:

1) Ionizing radiation protectants to protect skin, and to protect against mucositis, the effects of whole body radiation, and radiation-induced hair loss. Administration in these situations may be accomplished either via topical application as an ointment, lotion, or cream, intravenously or orally by pill or lozenge.

2) Protectants against increased oxygen exposures so as to avoid, for example, pulmonary adult respiratory distress syndrome (ARDS).

3) Protectants against oxygen-induced lenticular degeneration and hyaline membrane disease in infants, and against oxidative stress-induced cataracts. The compounds may also be used to protect against oxidative stress in patients undergoing oxygen therapy or hyperbaric oxygen treatment. Administration under these circumstances may be accomplished via various routes including, for example, the use of eye drops, aerosol inhalation, or intravenous injection.

4) Reperfusion injury protectants effective in treating cardiovascular phenomena such as myocardial infarction and strokes, pancreatitis, or intestinal ulceration; to protect patients receiving organ transplants, and in organ preservation solutions.

5) Protectants for use in animal or plant cell culture media to prevent cytotoxicity due to excessive oxidation, for use in media designed for culturing aerobic microorganisms, for use in stabilizing labile chemical compounds which undergo spontaneous degradation by generating free radicals, for use in neutralizing free radicals which catalyze chain elongation during polymer formation, thereby terminating polymer elongation, and for use as a stabilizer for foods or food additives such as colors and flavors, especially in foods preserved via radiation treatment.

6) Biological antioxidants to protect humans and animals against agents such as the herbicide paraquat. In this circumstance, the pharmaceutical composition may be administered, for example, via inhalation as an aerosol to a subject exposed to paraquat. In addition, plants may be protected against such agents by, for example, spraying before or after exposure to such compounds.

7) Protectants against the cytotoxic effects of chemotherapeutic agents.

8) Protectants against mutagenic and carcinogenic agents. Administration in this situation or in 6, above, may be accomplished via oral ingestion, or parenterally.

9) Anti-inflammatory agents effective against arthritic conditions. For this purpose, the compositions may be administered parenterally, intra-articularly, or via oral ingestion.

10) Aging retardants. Administration for this purpose may be accomplished orally such as via a tablet supplement to the diet or parenterally.

11) Oral or intravenous agents inducing weight reduction.

These and other objects are accomplished by providing a biologically compatible composition, comprising: an effective amount of a compound of the formula wherein $R_1$ is $-CH_3$; $R_2$ is $-C_2H_5$, $-C_3H_7$, $-C_4H_9$, $-C_5H_{11}$, $-C_6H_{13}$, $-CH_2-CH(CH_3)_2$, $-CHCH_3C_2H_5$, or $-(CH_2)_7-CH_3$, or wherein $R_1$ and $R_2$ together form spirocyclopentane, spirocyclohexane, spirocycloheptane, spirocyclooctane, 5-cholestane, or norbornane; $R_3$ is $-O$. or $-OH$, or a physiologically acceptable salt thereof which has antioxidant activity; and a biologically acceptable carrier.

Compounds which may be useful in the present invention also include any compound having a group, or a salt thereof. These compounds can be represented broadly by the formula:

wherein $R_3$ is as defined above, and $R_4$ and $R_5$ combine together with the nitrogen to form a heterocyclic group. The atoms in the heterocyclic group (other than the N atom shown in the formula) may be all C atoms or may be C atoms as well as one or more N, O and/or S atoms. The heterocyclic group preferably has 5 or 6 total atoms. The heterocyclic group may be preferably a pyrrole, imidazole, oxazole, thiazole, pyrazole, 3-pyrroline, pyrrolidine, pyridine, pyrimidine, or purine, or derivatives thereof, for example.

Further compounds which may be useful in the present invention also include those wherein $R_4$ and $R_5$ themselves comprise a substituted or unsubstituted cyclic or heterocyclic groups.

Still further compounds which may be useful in the present invention also include oxazolidine compounds capable of forming an oxazolidine-1-oxyl.

Yet further compounds which may be useful in the present invention also include metal-independent nitroxides.

The present invention is also directed to methods for treating the deleterious effects of harmful oxygen-derived metabolic products, as listed above.

Physiologically acceptable salts include acid addition salts formed with organic and inorganic acids, for example, hydrochlorides, hydrobromides, sulphates such as creatine sulphate salts, phosphates, citrates, fumarates and maleates. The compounds of the invention have been shown to exhibit little or no in vitro cytotoxicity at concentrations of from 1–5 mM for 5 hours.

The compounds of the present invention can be used for the treatment of the toxic effects of oxidative stress in a variety of materials, cells and mammals including humans, domestic and farm animals, and laboratory animals such as hamsters, mice, rats, monkeys, etc. It is contemplated that the invention compounds will be formulated into pharmaceutical compositions comprising an effective antioxidant amount of the compounds of formula (I) and pharmaceutically acceptable carriers. An effective antioxidant amount of the pharmaceutical composition will be administered to the subject or organism, human, animal, or plant, in a manner which prevents the manifestations of oxidative stress. The amount of the compound (I) and the specific pharmaceutically acceptable carrier will vary depending upon the host and its condition, the mode of administration, and the type of oxidative stress condition being treated.

In a particular aspect, the pharmaceutical composition comprises a compound of formula (I) in effective unit dosage form. As used herein the term "effective unit dosage" or "effective unit dose" is denoted to mean a predetermined antioxidant amount sufficient to be effective against oxidative stress in vitro or in vivo. Pharmaceutically acceptable carriers are materials useful for the purpose of administering the medicament, which are preferably non-toxic, and may be solid, liquid or gaseous materials which are otherwise inert and medically acceptable, and are compatible with the active ingredients. The pharmaceutical compositions may contain other active ingredients such as antimicrobial agents and other agents such as preservatives.

These pharmaceutical compositions may take the form of a solution, emulsion, suspension, ointment, cream, aerosol, granule, powder, drops, spray, tablet, capsule, sachet, lozenge, ampoule, pessary, or suppository. They may be administered parenterally, intramuscularly or subcutaneously, intravenously, intra-articularly, transdermally, orally, buccally, as a suppository or pessary, topically, as an aerosol spray, or drops.

The compositions may contain the compound in an amount of from 0.1%–99% by weight of the total composition, preferably 1 to 90% by weight of the total composition. For intravenous injection, the dose may be about 0.1 to about 300 mg/kg/day. If applied topically as a liquid, ointment, or cream, the compound may be present in an amount of about 0.01 to about 100 mg/ml of the composition. For inhalation, about 0.1 to about 200 mg/kg body weight of the compound should be administered per day. For oral administration, the compound should be administered in an amount of about 0.1 to about 300 mg/kg/day.

The invention also provides a method for treating the effects of oxidative stress due to the production of harmful oxygen-derived species which comprises administering an effective antioxidant amount of the above-mentioned compound to a organism, material, mammal or human susceptible to oxidative stress. Such stress includes that due to oxidizing agents, increased oxygen exposure, oxygen-induced degeneration or disease, reperfusion injury, ionizing radiation, carcinogenic, chemotherapeutic, or mutagenic agents, aging, or arthritis.

Reperfusion injury may include myocardial infarction, strokes, pancreatitis, and intestinal ulceration, while oxidative stress due to increased oxygen exposure includes pulmonary adult respiratory distress syndrome. Other oxidative stresses amenable to treatment with the compounds of the instant invention include oxygen-induced lenticular degeneration, cataracts or hyaline membrane disease in infants, or oxidative stress occurring during oxygen therapy or hyperbaric oxygen treatment.

Finally, in a further aspect of the invention, the compound of the instant invention can be used to prolong the storage life of human or animal cells, tissues, or organs by contacting these materials with a storage solution containing an effective amount of such compound, or to induce weight reduction in humans or animals.

The terms "biologically compatible" refer to a composition which does not cuase any adverse effects to an organism to which it is applied. The composition is preferably free of toxic substances or other substances which would render it unsuitable for the intended use.

The term "parenteral" includes an administration by injection such as intravenous, intramuscular, or subcutaneous.

DESCRIPTION OF THE PREFERRED EMBODIMENTS

EXAMPLE 1

Synthesis and SOD-like activity of oxazolidine derivatives in vitro.

Desferrioxamine (DF) was a gift from Ciba Geigy; hypoxanthine (HX) was purchased from Calbiochem-Boehringer Co.; 2,2,6,6-tetramethylpiperidine-1-oxyl (TEMPO), 4-hydroxy-2,2,6,6-tetramethylpiperidine-1-oxyl (TEMPOL), 4-hydroxypyrazolo[3,4,-d]-pyrimidine (allopurinol), p-toluene sulfonic acid, 2-amino-2-methyl-1-propanol, 2-butanone, and cyclohexanone were purchased from Aldrich Chemical Co.; trioxalato chromiate(III) (CrOx) was purchased from Pfaltz and Bauer, Inc., and recrystallized; xanthine oxidase (EC 1.2.3.2. xanthine: oxygen oxidoreductase) grade III from buttermilk, superoxide dismutase (SOD), and grade V ferricytochrome c were obtained from Sigma. $H_2O_2$ was bought from Fisher Scientific Co. XO was further purified on a G25 sephadex column. All other chemicals were prepared and used without further purification. Distilled-deionized water was used throughout all experiments.

CHD, 2-spirocyclohexane doxyl (2-spirocyclohexane-5,5-dimethyl-3-oxazolidinoxyl) and OXANO, 2-ethyl-2,5,5-trimethyl-3-oxazolidine-1-oxyl as well as other nitroxides were synthesized as described by Keana et al (J. Am. Chem. Soc., 89, 3055–3056, 1967). For the general synthesis of the cyclic amines, the appropriate starting ketone was reacted with 2-amino-2-methyl-1-propanol in benzene in the presence of catalytic amounts of p-toluene sulfonic acid. As the cyclic structure formed, water was eliminated. The volume of water collected in a Dean Stark apparatus was monitored and used to gauge the reaction progress. The amines thus produced were purified through fractional distillation under reduced pressure, characterized by 220 MHz $^1H$ NMR, IR, UV, either EI or CI mass spectroscopy, and subsequently oxidized to the corresponding nitroxides using m-chloroperbenzoic acid. The nitroxides were purified by silica flash chromatography (Still et al, J. Org. Chem., 43, 2923–2925, 1978). Water/octanol ratios were determined by placing a quantity of nitroxide in water+octanol within a separatory funnel. The mixture was shaken thoroughly and allowed to separate for 15 min, whereupon aliquots were taken from both fractions and the ratio of nitroxide distribution was determined using electron paramagnetic resonance (EPR) spectroscopy, by comparing the intensities of signal obtained under $N_2$.

To check whether oxazolidinoxyl derivatives other than OXANO manifest SOD-like activity, several nitroxides having different ring substituents were synthesized. Table 1A shows representative synthesized nitroxides with accompanying physical characteristics.

TABLE 1A

Five-Membered Oxazolidine-1-oxyl (Dozyl)

| Nitroxide notation | Ring substituents | | Yield (%) | Partition[#] coefficient |
|---|---|---|---|---|
| | $R_1$ | $R_2$ | | |
| I  OXANO | $CH_3$ | $C_2H_5$ | 42 | 10 |
| II | $CH_3$ | $C_5H_{11}$ | 52 | 145 |
| III | $CH_3$ | $C_4H_9$ | 49 | 58 |
| IV  CHD | spirocyclohexyl | | 77 | 80 |
| V | $CH_3$ | $C_6H_5$ | 22 | 720 |

[#]Octanol:water

Exposure of these 5-membered cyclic nitroxides to $O_2^-$ flux formed by HX/XO resulted in a decrease in their EPR signal, as previously found for OXANO (Samuni et al, Free Rad. Biol. Med., 6, 141–148, 1989). For EPR experiments, samples (0.05–0.1 ml) either of solutions of chemicals or cell suspensions were drawn by a syringe into a gas-permeable teflon capillary of 0.8 mm inner diameter, 0.05 mm wall thickness (Zeus Industrial Products, Inc. Raritan, N.J.). Each capillary was folded twice, inserted into a narrow quartz tube which was open at both ends (2.5 mm ID), and then placed horizontally into the EPR cavity. During the experiments, gases of desired compositions were blown around the sample without having to disturb the alignment of the tube within the EPR cavity. EPR spectra were recorded in a Varian E4 (or E9) X-band spectrometer, with field set at 3357G, modulation frequency of 100 KHz, modulation amplitude of 1G and non-saturating microwave power. The EPR spectrometer was interfaced to an IBM-PC through an analog-to-digital converter and a data translation hardware (DT2801) and the spectra were digitized using commercial acquisition software, enabling subtraction of background signals. To study the kinetics of the spin-loss, the spectra were deliberately overmodulated, and the magnetic field was kept constant while the intensity of the EPR signal was followed.

After terminating the HX/XO reaction by allopurinol, the nitroxide spin-loss was reversed by adding 0.5 mM ferricyanide, indicating that $O_2^-$ reduces the nitroxide to its respective hydroxylamine (Samuni et al, Free Rad. Biol. Med., 6, 141–148, 1989). On the other hand, no effect of $O_2^-$ on the EPR signal of 6-membered ring nitroxides such as TEMPO and TEMPOL was detectable (see Table 1B).

TABLE 1B

Kinetic Data: SOD-like Activity of 5- and 6-Membered Cyclic Nitroxides
Chemical Structure

| Nitroxide notation | TEMPOL | TEMPO | OXANO | CHD |
|---|---|---|---|---|
| Steady state EPR signal (%)[a] | 100 | 100 | 50 | 30 |
| $kR'RNO + O_{1/2}$ $(M^{-1}s^{-1})$[b] | $3.4 \times 10^5$ | $1.3 \times 10^6$ | $1.1 \times 10^3$ | $3.5 \times 10^3$ |

[a]Steady-state EPR signal of nitroxides (% from total R'RNO + R'RNOH) after exposure to 5 mM HX + 0.03 U/ml XO in air-saturated PBS pH 7.2.
[b]Rate constants were determined at low ionic strength (10 mM HEPES), pH 7.0, and 22° C.

The failure of superoxide to affect TEMPO and TEMPOL apparently suggested that 6-membered cyclic nitroxides lack SOD-like activity. As a further check, the reaction of representatives of both 5- and 6-membered cyclic nitroxides with $O_2^-$ was studied. The SOD-inhibitable ferricytochrome c reduction assay (Fridovich, *Handbook of Methods for Oxygen Radical Research*, 213–215, 1985) was used to determine rate constants of reaction with $O_2^-$. Superoxide radicals were generated at 25° C. in aerated phosphate buffer (50 mM) containing 50 µM DTPA, 5 mM HX, and 10–50 µM ferricytochrome c (with or without 65 U/ml catalase). The reaction was started by adding 0.01 U/ml XO and the rate of ferricytochrome c reduction, in the absence (V) and in the presence (v) of various nitroxides, was spectrophotometrically followed at 550 nm. Both reference and sample cuvettes contained all the reagents, with the reference cuvette containing 100 units/ml SOD, thereby eliminating spurious reactions from interfering with the determination of rate constants. Data were analyzed by plotting V/v as a function of [nitroxide] and $k_1$ was calculated knowing $k_{CytC+superoxide}$, according to: $(V/v)-1 = k_1 \times [nitroxide]/k_{CytC+superoxide} \times [Cyt-c^{III}]$.

Via this assay, all the nitroxides listed below have been shown to function as superoxide dismutase mimics.

TABLE 2

Physical data of 2-substituted-5,5-dimethyl-3-oxazolidines.
Generalized Structure, R groups shown in table.

| Oxazolidine (A-I) | R1 | R2 | Yield % | b.p. C (760 mmHg) |
|---|---|---|---|---|
| A | CH3 | C2H5 | 42 | 162–165 |
| C | CH3 | C3H7 | 36 | 169–170 |
| D | CH3 | C4H9 | 71 | 185–188 |
| E | CH3 | C5H11 | 52 | 204–205 |
| F | CH3 | C6H13 | 54 | 225–230 |
| G | CH3 | CH2CH(CH3)2 | 49 | 168–170 |
| H | CH3 | CHCH3C2H5 | 25 | 184–185 |
| I | CH3 | (CH2)7CH3 | 57 | 165–166 |

| Oxazolidine (J-R) | Alicyclic substituent | | Yield % | b.p. C (760 mmHg) |
|---|---|---|---|---|
| J | spirocyclopentane | | 61 | 133–135 (75) |
| K | spirocyclohexane | | 77 | 208–211 (760) |
| L | spirocycloheptane | | 50 | 145–147 (35) |
| M | spirocyclooctane | | 40 | 234–235 (760) |
| N | 5-cholestane | | — | — |
| O | norbornane | | 53 | 178–180 (80) |

The rate constants of the synthetic nitroxides' reaction with $O_2$ at low ionic strength (10 mMHEPES) and pH 7.0 ranged from $1.1 \times 10^3$ to $1.3 \times 10^6 M^{-1} s^{-1}$, as compared with $2.3 \times 10^9 M^{-1} s^{-1}$ for $k_{cat}$ of native SOD.

None of the nitroxides shown (in the last two tables) exhibited cytotoxicity determined by clonogenic assay in V79 cells exposed for 1 h at 5 mM. For subsequent studies, the most lipophilic nitroxide, CHD, and the most hydrophilic one, TEMPOL, were chosen.

EXAMPLE 2

Nitroxide Intracellular Localization.

Figure 1A:
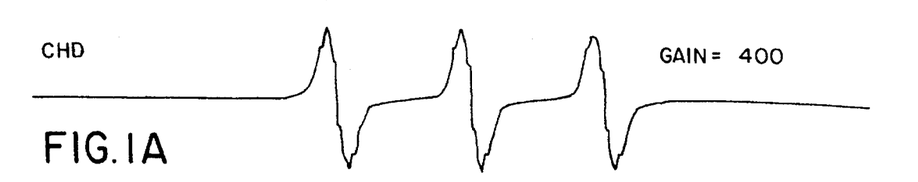
FIG. 1 shows EPR spectra of CHD and TEMPO demonstrating the partitioning of each nitroxide (1 mM) in both the intra- and extra-cellular space of V79 cells. The EPR signal intensity of the total concentration of CHD (intra- and extra-cellular) in $6.4 \times 10^7$ V79 cells/ml traces (A and C) and in the presence of 110 mM trioxalatochrmiate (CrOx) (traces B and D). The gains for individual spectra are as cited in the individual figures.
Figure 1B:
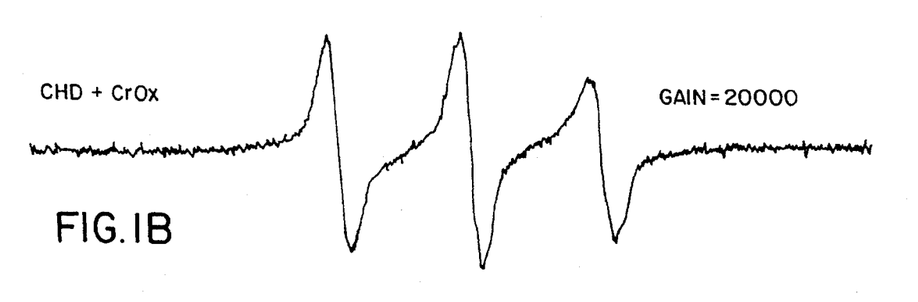
Figure 1C:
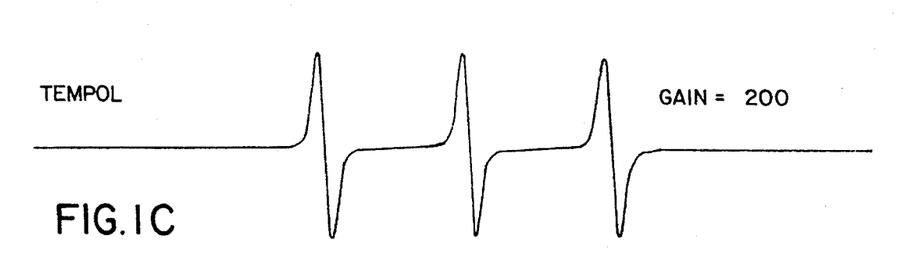
Figure 1D:
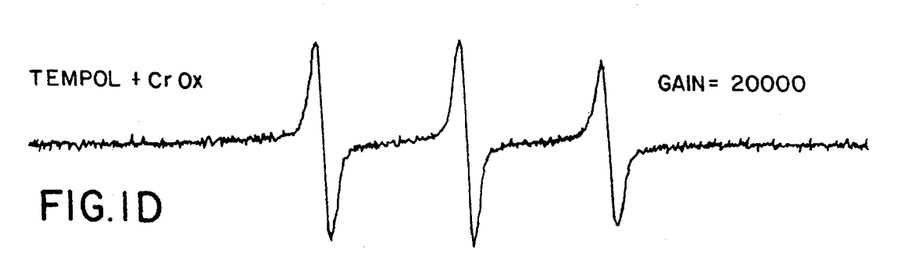
Figure 1E:
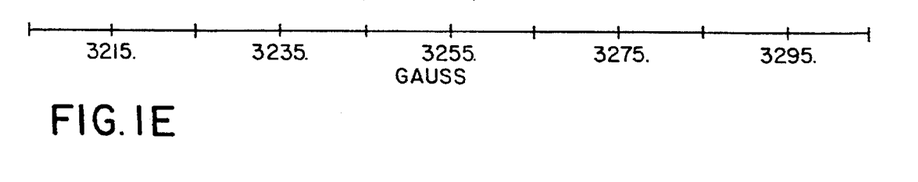

FIG. 1A and C illustrate the EPR signal from 1 mM CHD and TEMPOL, respectively, suspended with $6.4 \times 10^7$ V79 cells/ml. This EPR signal represents the total concentration of intra- and extra-cellular CHD. Trioxalato-chromiate is a paramagnetic broadening agent which remains excluded from the intracellular volume space and causes the EPR signal from extracellular species to become non-detectable (Lai, Biophys. J., 52, 625–628, 1987). When cells were added to CHD or TEMPOL in the presence of 110 mM trioxalatochrmiate, a much smaller yet observable intracellular signal was detected as shown in FIG. 1B and D. The observable line broadening and loss of the hyperfine structure of the intracellular signal indicate that CHD, though not the TEMPOL, has decreased freedom of motion (anisotropy) within the intracellular environment and is located primarily in a membranous compartment as can be anticipated based on the difference between their lipophilicities.

EXAMPLE 3

Protection of Cells Against Oxidative Damage.

Chinese hamster V79 cells were grown in F12 medium supplemented with 10% fetal calf serum, penicillin, and streptomycin. Survival was assessed in all studies by the clonogenic assay. The plating efficiency range between 80–90%. Stock cultures of exponentially growing cells were trypsinized, rinsed, and plated ($5 \times 10^5$ cells/dish) into a number of 100 mm petri dishes and incubated 16h at 37° C. prior to experimental protocols. Cells were exposed for 1h at 37° C. to either 0.5 mM hypoxanthine (HX)+0.05 U/ml of xanthine oxidase (XO) for varying lengths of time, or to $H_2O_2$ at different concentrations. To assess possible modulation in cytotoxicity, catalase, 100 U/ml; SOD, 100 µg/ml; DF, 500 µM; and 5 mM of each of the nitroxides from Table 1 were added to parallel cultures. CHD was prepared in a stock solution in ethanol and diluted into medium such that the final concentration was 5 mM. This resulted in a final concentration of 1% ethanol in the medium which was not cytotoxic and did not influence the cellular response to HX/XO or $H_2O_2$. TEMPOL is water soluble and was prepared directly in tissue culture medium. Neither catalase, SOD, DF, CHD, nor TEMPOL were cytotoxic alone in the concentrations used. DF was added either 2 h prior to or during treatment while the other agents were present only during HX/XO or $H_2O_2$ treatment. Following treatment, cells were rinsed, trypsinized, counted, and plated for macroscopic colony formation. For each dose determination cells were plated in triplicate and the experiments were repeated a minimum of two times. Plates were incubated 7 days, after which colonies were fixed with methanol/acetic acid, stained with crystal violet, and counted. Colonies containing >50 cells were scored. Error bars represent S.D. of the mean and are shown when larger than the symbol.

Some studies required exposure to $H_2O_2$ under hypoxic conditions. For these studies, cells dispersed in 1.8 ml of medium were plated into specially designed glass flasks (Russo et al, Radiat. Res., 103, 232–239, 1985). The flasks were sealed with soft rubber stoppers, and 19-gauge needles were pushed through to act as entrance and exit ports for a humidified gas mixture of 95% nitrogen/5% $CO_2$ (Matheson Gas Products). Each flask was also equipped with a ground glass side arm vessel which when rotated and inverted could deliver 0.2 ml of medium containing $H_2O_2$ at a concentration which when added to the cell monolayer resulted in final concentration of $H_2O_2$ of 600 µM. Stoppered flasks were connected in series and mounted on a reciprocating platform and gassed at 37° C. for 45 min. This gassing procedure results in an equilibrium between the gas and liquid phase (in both the medium over the cell monolayer and in the solution in the sidearm) and yielded oxygen concentrations in the effluent gas phase of <10 ppm as measured by a Thermox probe (Russo et al, Radiat. Res., 103 232–239, 1985). After 45 min of gassing, the hypoxic H2O2 solution was added to the cell monolayer culture. The cells were exposed to $H_2O_2$ for 1 h under hypoxic conditions. $N_2$ gas flow was maintained during the $H_2O_2$ exposure. In parallel flasks, DF and CHD were added as described above, and were present during the entire gassing procedure. Following treatment, cell survival was assessed as described above.

Hydrogen peroxide was assayed using a YSI Model 27 Industrial Analyzer (Yellow Springs Instruments) equipped with a selective electrode for $H_2O_2$. For analysis of cellular preparations, the cells, except during the brief time required for removal of aliquots for analysis, were kept in T25 culture flasks maintained at 37° C. in complete medium (pH 7.2). Aliquots of 25 µl were sampled from the reaction or cell preparation system at varying time points and injected into the analyzer. [$H_2O_2$] was determined after calibrating the instrument with known concentrations of $H_2O_2$. The concentrations of standard $H_2O_2$ solutions were calibrated using iodometric assay (Hochanadel, J. Phys. Chem., 56, 587–594, 1952).

Figure 2:
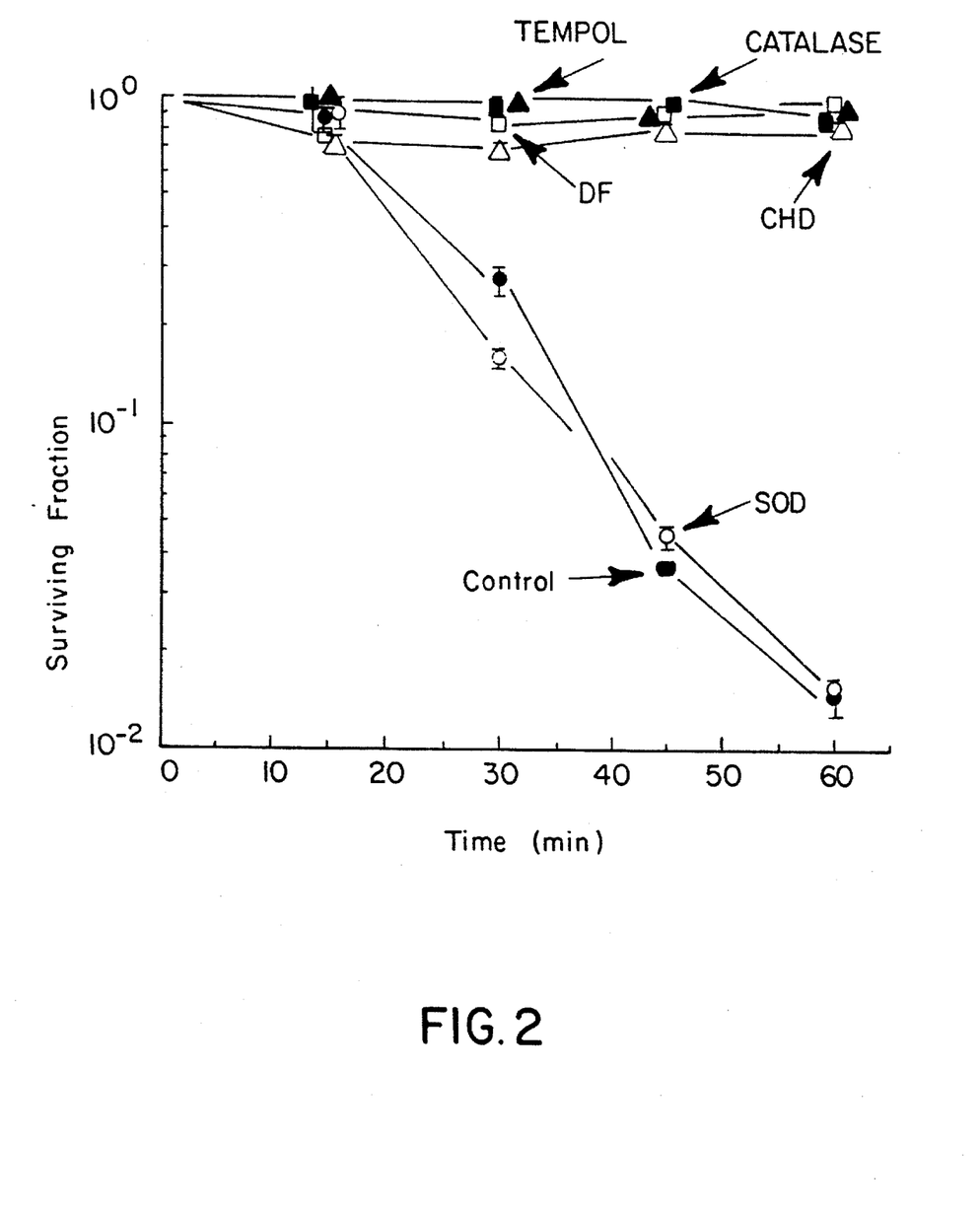
FIG. 2 shows a survival curve for Chinese hamster V79 cells exposed to HX/XO (hypoxanthine/xanthine oxidase) in the presence of various additives, including the nitroxides CHD and TEMPOL, which fully protected the cells. Chinese hamster V79 cells in full medium at 37° C. were exposed to 0.05 U/ml XO+0.5 mM HX for various time periods in the presence of various additives: (●), control, no additives; (■), 100 U/ml catalase; (○), 100 U/ml SOD; (□), 500 μM DF (desferrioxamine), preincubated for 2 h with the cells prior to addition of XO; (Δ), 5 mM CHD; (▲), 5 mM TEMPOL.

To expose the cells to oxidative stress they were incubated with HX/XO. FIG. 2 shows a survival curve for cells exposed to HX/XO. Cell survival was not altered when SOD was present during the HX/XO exposure. In contrast, 5 mM CHD or TEMPOL fully protected the cells. The other nitroxides, presented in Table I, afforded similar protection (data not shown). FIG. 2 also shows that either catalase or DF provides complete protection from HX/XO-derived damage. Complete protection by DF required a 2 h preincubation with DF before cells were exposed to HX/XO, whereas DF addition simultaneously with HX/XO offered only partial protection (data not shown).

Figure 3:
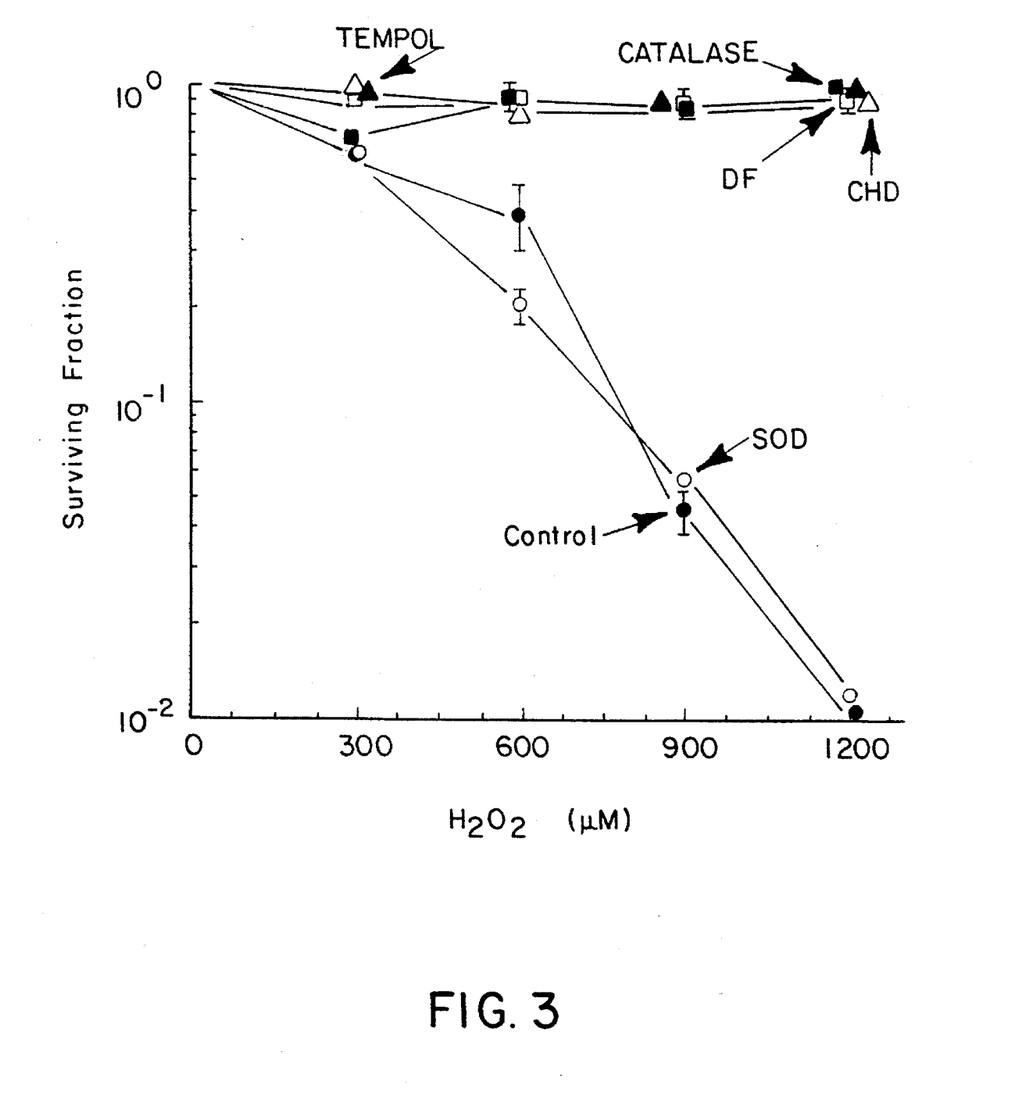
FIG. 3 shows a survival curve for cells exposed to $H_2O_2$ in the presence of various additives, including the nitroxides CHD and TEMPOL, which fully protected the cells. The effect of various agents on cell survival was measured by clonogenic assay of Chinese hamster V79 cells exposed in full medium at 37° C. to various concentrations of $H_2O_2$ for 1 h; (●), control, no additives; (■), 100 U/ml catalase; (○), 100 μg/ml SOD; (□), 500 μM DF, preincubated 2 h with the cells prior to $H_2O_2$ addition; (Δ), 5 mM CHD; (▲), 5 mM TEMPOL.
Figure 4:
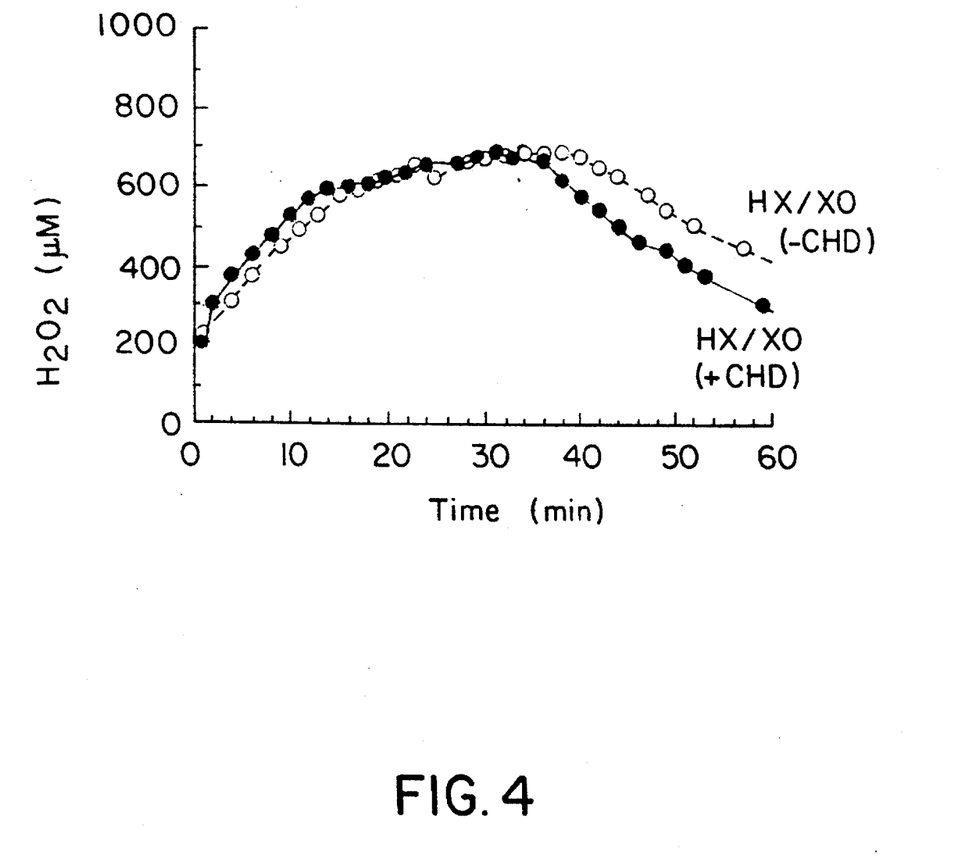
FIG. 4 shows the effect of nitroxide on the accumulation and decay of $H_2O_2$ in a tissue culture of cells exposed to HX/HO. Chinese hamster V79 cells were plated in full medium and incubated at 37° C. with 5 mM HX+0.04 U/ml XO, sampled at various time points, and assayed for $H_2O_2$ using a hydrogen peroxide selective electrode.

One interpretation of the data shown in FIG. 2 is that $H_2O_2$ is the principal cytotoxic species produced by the HX/XO system (Link & Riley, Biochem. J., 249, 391–399, 1988). This assumption is based on the fact that extracellular catalase provided complete protection from HX/XO (FIG. 2). To test if cell protection by the SOD-mimic resulted from detoxifying $H_2O_2$, cells were exposed to $H_2O_2$ as shown in FIG. 3. The results of these experiments were identical to those shown in FIG. 2, in that SOD did not protect, but catalase, DF, TEMPOL, and CHD provided complete protection against $H_2O_2$ cytotoxicity. At this point it was questioned if CHD might have other features apart from acting as a SOD mimic, namely, whether CHD affects $H_2O_2$ concentration. FIG. 4 shows the concentration of $H_2O_2$ in tissue culture exposed to HX/XO. With time there was a build-up followed by a slow decline in $[H_2O_2]$. The presence of CHD did not significantly alter the pattern of $H_2O_2$ generation by HX/XO. Thus, the cellular protection afforded by CHD to HX/XO and $H_2O_2$ could not be attributed to a direct reaction of CHD with $HO_2$.

Even with direct exposure of cells to $H_2O_2$, there is the possibility that superoxide could be produced intracellularly as a result of the $H_2O_2$ a treatment. If superoxide were produced intracellularly, CHD protection of cells from HX/XO and $H_2O_2$ might be expected, given the findings that CHD can penetrate intracellular spaces as shown in FIG. 1. To test if the cytoprotection provided by CHD was solely a result of its reaction with superoxide, CHD effectiveness was examined when $H_2O_2$ was applied to cells incubated in a hypoxic environment, conditions in which the chance for superoxide formation would be significantly limited. As is seen in FIG. 5, CHD protects against $H_2O_2$ cytotoxicity even under hypoxic conditions.

Figure 5:
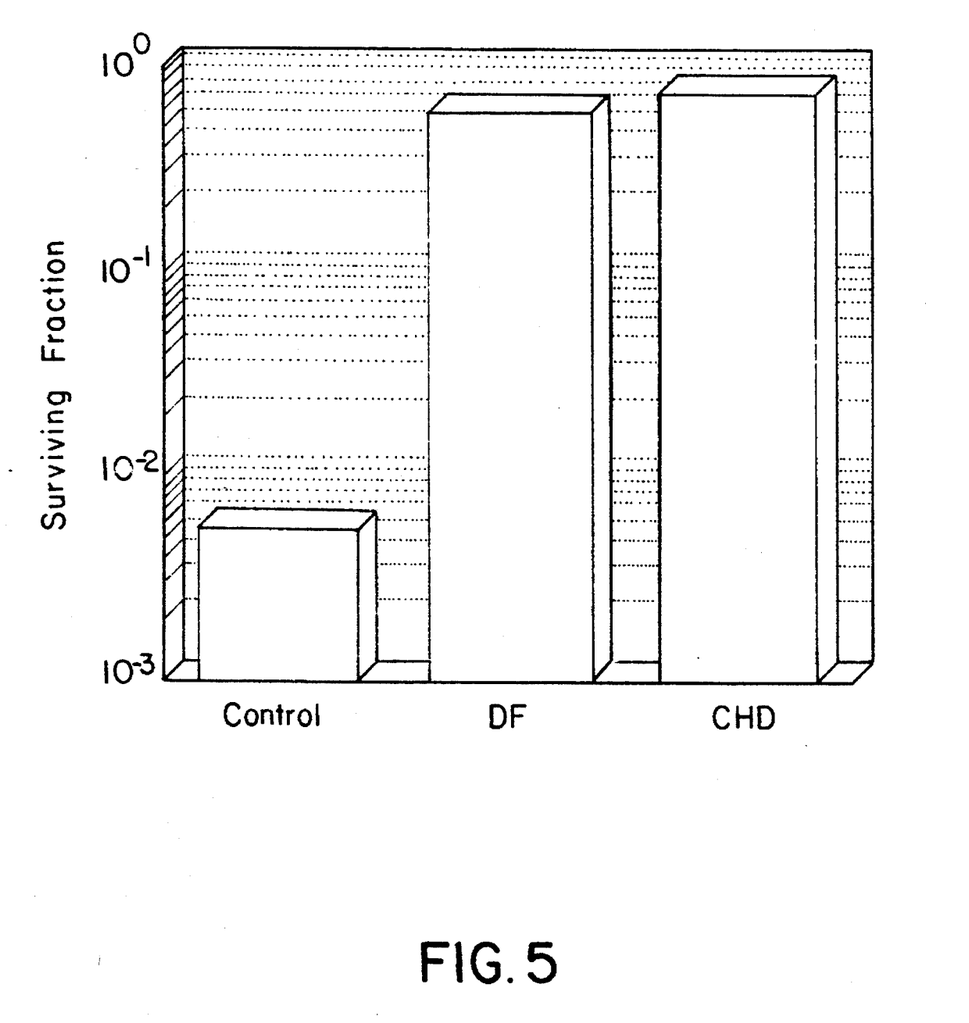
FIG. 5 shows the survival of Chinese hamster V79 cells exposed to 600 μM $H_2O_2$±DF or CHD in full medium at 37° C. for 1 h under hypoxic conditions.
Figure 6A:
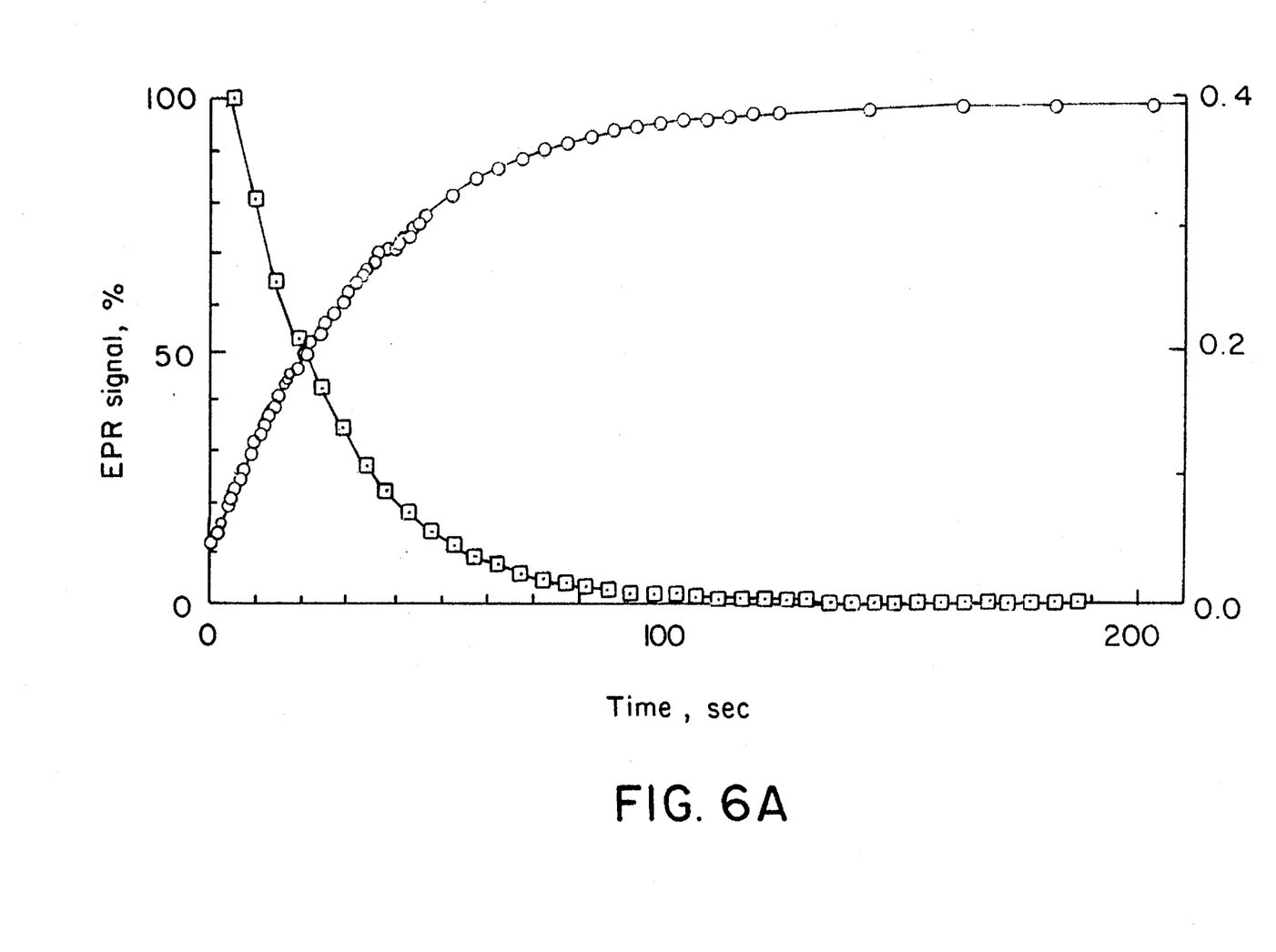
FIG. 6 shows the reaction between CHD and DNA-Fe(II): CHD in 50 mM MOPS buffer pH 7.0 was anoxically mixed at 22° C. with DNA-Fe(II). All solutions always contained 0.1 mg/ml Salmon DNA. The appearance of DNA-Fe (III) was spectrophotometrically monitored at 353 nm, whereas the spin-loss of CHD was monitored by following its EPR signal. To study the time-dependence of $\Delta OD_{353nm}$ (○), 1 mM CHD was mixed with 0.1 mM Fe(II). To follow the spin-loss of CHD (□), 1 mM Fe(II) was mixed with 0.1 mM CHD. Inset: Time-dependence of ln{EPR signal} (□); and of ln{$(OD_\infty - OD_t)$} (○).
Figure 6B:
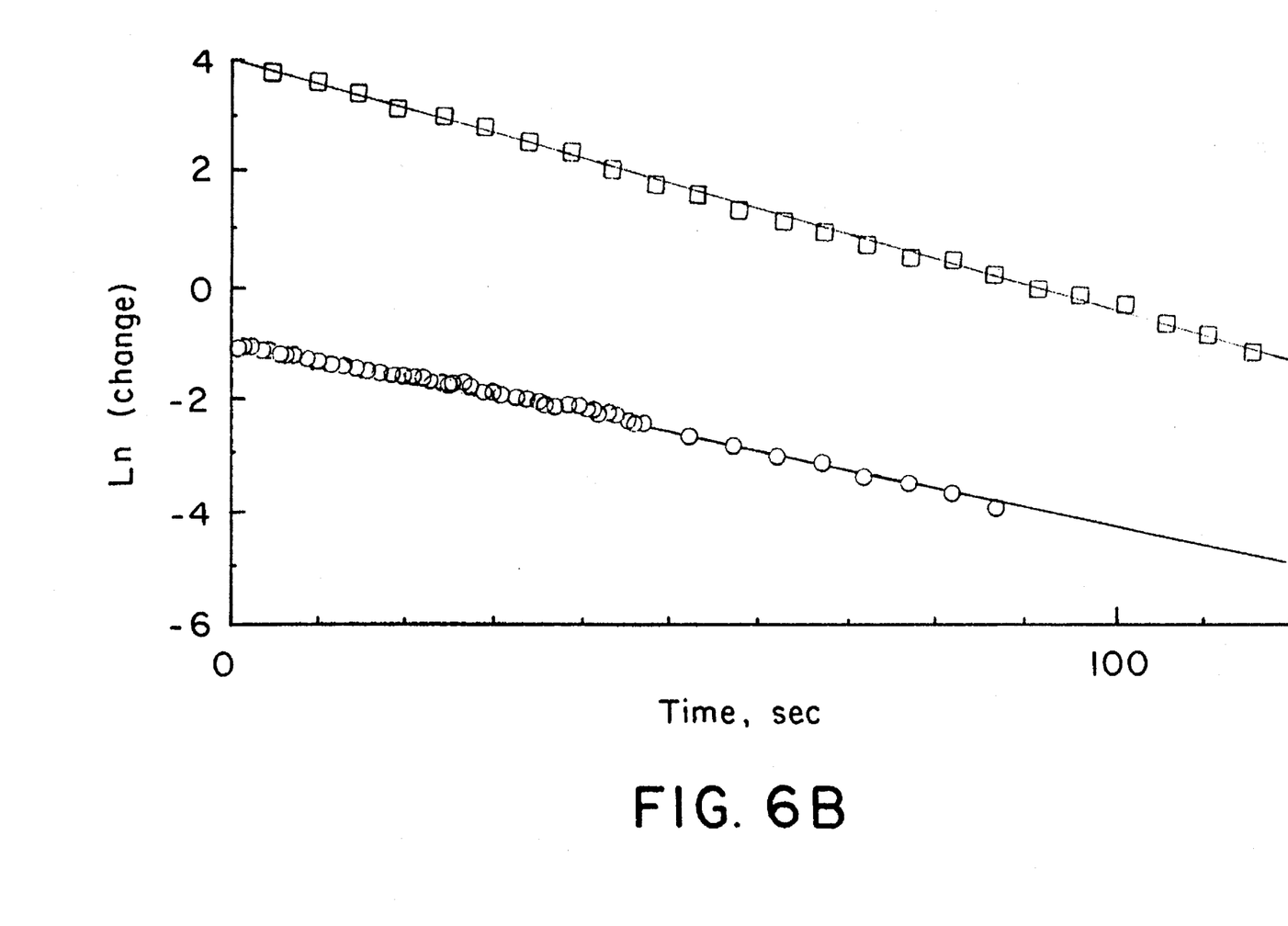
Figure 7A:
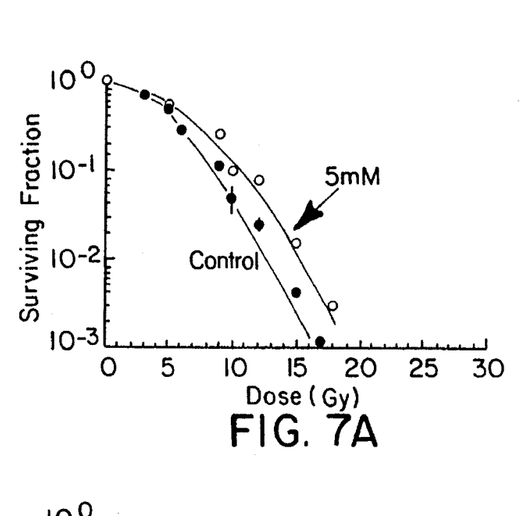
FIG. 7 shows the clonogenic survival of Chinese hamster V79 cells treated with varying concentrations of TEMPOL 10 min prior to radiation.
Figure 7B:
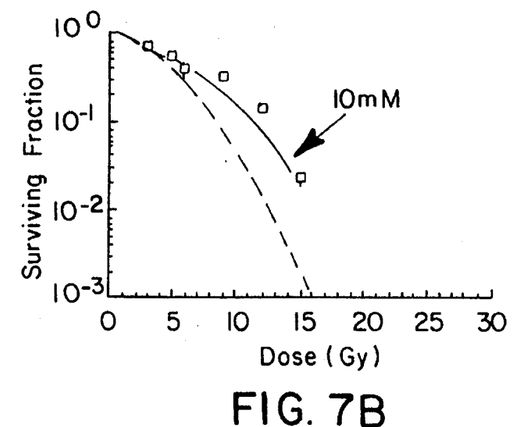
Figure 7C:
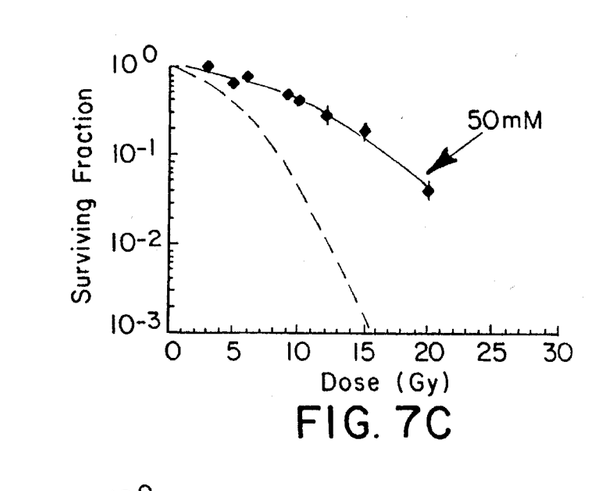
Figure 7D:
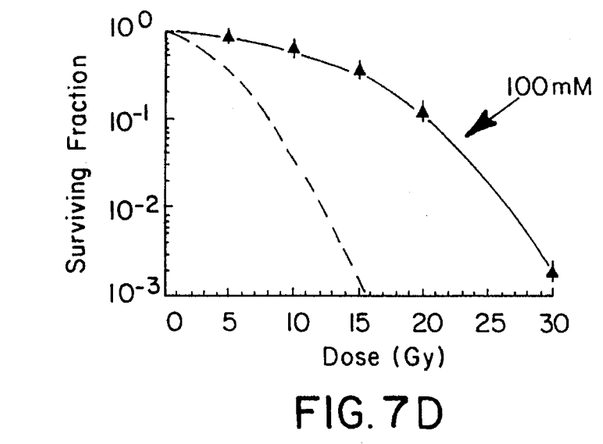

FIG. 5 also shows that DF provides complete protection to $H_2O_2$ cytotoxicity under hypoxic conditions. The pattern of DF protection shown in FIGS. 2, 3, and 5 suggested that the cytotoxicity of HX/XO and $H_2O_2$ may directly involve intracellular reduction of $H_2O_2$ by ferrous ion to produce the highly toxic .OH. It was also questioned whether the aerobic and hypoxic protection by CHD to $H_2O_2$ exposure was a result of CHD directly accepting electrons from ferrous ions, thereby preventing generation of .OH. Because cellular iron is chelated, the possible reaction of nitroxide with chelated iron(II) was examined by repeating the experiment in the presence of DNA. To study the possibility of nitroxide-induced oxidation of transition metals, CHD was hypoxically mixed with iron(II) in the presence of 0.1 mg/ml Salmon DNA. Consequently, DNA-Fe(III) was formed and the nitroxide EPR signal disappeared. The reaction kinetics were investigated by maintaining either CHD or Fe(II) in excess while the absorbance due to DNA-Fe(III) and the nitroxide spin-loss were monitored respectively (FIG. 6). Both the decay of the EPR signal and the appearance of the $OD_{353nm}$ obeyed pseudo $1^{st}$ order kinetics from which the $2^{nd}$ order reaction rate constant was calculated as 44 $M^{-1}s^{-1}$ or 33 $M^{-1}s^{-1}$ using the data from EPR or optical absorption, respectively. When TEMPOL was hypoxically mixed with DNA-Fe(II), a similar reaction took place having a $2^{nd}$ order reaction rate constant of 40 $M^{-1}s^{-1}$. The spin-loss was completely reversed by adding 2 mM ferricyanide, thus indicating that DNA-Fe(II) reduced the respective nitroxide to its hydroxylamine.

EXAMPLE 4

In Vitro and In Vivo Protection Against Ionizing Radiation by Nitroxide.

Chinese hamster V79 cells were treated with varying concentrations of TEMPOL 10 min prior to irradiation. The clonogenic survival compared to control cells is shown in FIG. 7. The extent of protection for 100 mM TEMPOL was approximately 2.5 fold.

Figure 8:
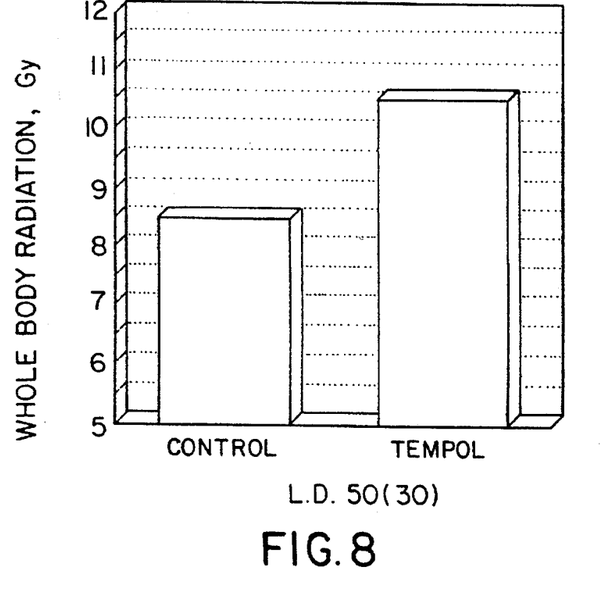
FIG. 8 shows the protection afforded whole animals treated with TEMPOL prior to whole body irradiation. Six week old female C3H mice were given 275 mg/kg TEMPOL intraperitoneally 10 mins prior to irradiation with 3 Gy to 13 Gy. Controls were given saline.

The protection afforded whole animals by TEMPOL was evaluated in six week, old female C3H mice given 275 mg/kg TEMPOL intraperitoneally 10 min prior to whole body radiation doses ranging from 3 Gy to 13 Gy. Controls were given saline. Survival was recorded 30 days after exposure to radiation. The $LD_{50(30)}$ refers to that dose of radiation at which 50% of the mice survived 30 days after exposure. As can be seen in FIG. 8, mice treated with TEMPOL had an approximately 25% higher $LD_{50(30)}$, demonstrating protection from whole body radiation and no toxicity.

The above results demonstrate that TEMPOL provides radio-protection at both the in vitro and in vivo level.

EXAMPLE 5

Nitroxide-Induced Weight Loss in Animals.

Figure 9:
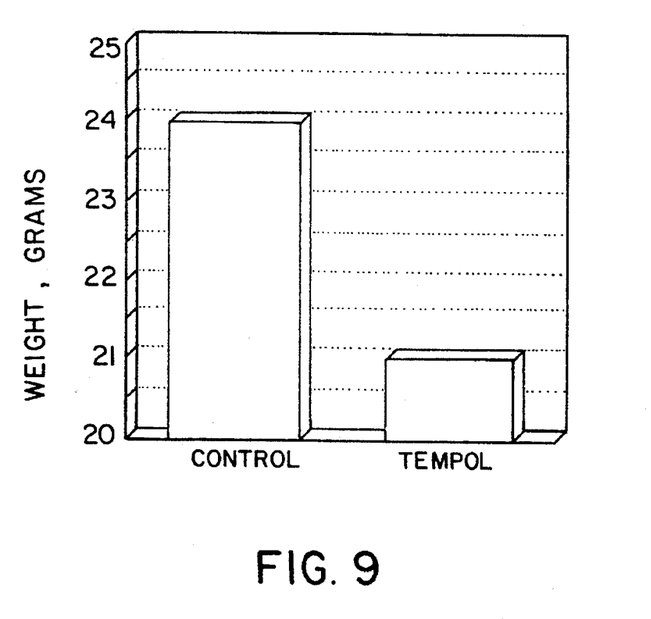
FIG. 9 shows the average weights of control and TEMPOL treated mice.

Six week old female C3H mice (6 animals in each group) were allowed to drink an unlimited supply of water alone (control) or 4 -hydroxy tempo (TEMPOL) dissolved in water at a concentration of 10 mg per ml. Chronic oral administration (>3 weeks) results in no apparent toxicity to the animals, but a reduction of weight compared to controls by 12.5% as shown in FIG. 9. Thus, nitroxide given over extended periods appears to cause weight loss in animals.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A pharmaceutical composition, comprising an antioxidative stress effective amount of a compound selected from the group consisting of a metal-independent nitroxide, an oxazolidine compound capable of forming an oxazolidine-1-oxyl, and a physiologically acceptable salt of either of the foregoing, and a biologically acceptable carrier, wherein said pharmaceutical composition is in a form selected from the group consisting of an emulsion, suspension, ointment, cream, aerosol, granule, powder, spray, tablet, capsule, sachet, lozenge, ampoule, pessary, and suppository, and wherein said effective amount of said compound is sufficient to protect biological material from oxidative stress.

2. The pharmaceutical composition of claim 1, wherein the compound has the formula:

wherein $R_3$ is selected from the group consisting of —O. and —OH, and $R_4$ and $R_5$ combine together with the nitrogen to form a heterocyclic group, or wherein $R_4$ and $R_5$ themselves comprise a substituted or unsubstituted cyclic or heterocyclic group, or a physiologically acceptable salt thereof.

3. The pharmaceutical composition of claim 1, wherein the compound is present in an amount of from to 1 to 90% by weight of the total composition.

4. The pharmaceutical composition of claim 1, wherein said physiologically acceptable salt is selected from the group consisting of a hydrochloride, hydrobromide, sulphate, phosphate, citrate, fumarate, maleate and mixtures thereof.

5. The pharmaceutical composition of claim 1, wherein said biologically acceptable carrier is a non-toxic gas.

6. The pharmaceutical composition of claim 1, further comprising an antimicrobial agent and/or a preservative.

7. The pharmaceutical composition of claim 1, in a form capable of being administered, transdermally, orally, bucally, or as a suppository, a pessary, an aerosol, or drops.

8. The pharmaceutical composition of claim 1, wherein said compound is present in an amount of from 0.1%–99% by weight of the total composition.

9. The pharmaceutical composition of claim 1, wherein the carrier is an ointment or a cream.

10. The pharmaceutical composition of claim 1, wherein the compound is 4-hydroxy-2,2,6,6-tetramethylpiperidine-1-oxyl, the compound is present in an amount of from about 0.01 to about 100 mg/ml of the total composition, and the carrier is an ointment or a cream.

11. The pharmaceutical composition of claim 1, wherein said pharmaceutical composition is a topical composition.

12. A method for treating the effects of oxidative stress due to the production of harmful free radical species, comprising administering a composition comprising an anti-oxidative stress effective amount of a compound selected from the group consisting of the oxidized form of a metal-independent nitroxide, the oxidized form of an oxazolidine compound capable of forming an oxazolidine-1-oxyl, and a physiologically acceptable salt thereof, to an organism or biological material susceptible to oxidative stress.

13. The method of claim 12, wherein the oxidative stress is due to the formation of free radicals by an oxidizing agent, increased oxygen exposure, oxygen therapy, hyperbaric oxygen treatment, oxygen-induced degeneration or disease, reperfusion injury, ionizing radiation, a carcinogenic agent, a chemotherapeutic agent, a mutagenic agent, aging, or arthritis.

14. The method of claim 13, wherein the oxidative stress is due to reperfusion injury.

15. The method of claim 13, wherein the oxidative stress is due to increased oxygen exposure associated with pulmonary adult respiratory distress syndrome.

16. The method of claim 12, wherein the effect of oxidative stress is oxygen-induced lenticular degeneration, cataracts, or hyaline membrane disease in infants.

17. The method of claim 12, wherein the organism is a mammal.

18. The method of claim 12, wherein the compound is administered as a pharmaceutical composition in a form selected from the group consisting of a solution, emulsion, suspension, tablet, capsule, sachet, lozenge, ampoule, ointment, cream, aerosol, powder, granule, eye drops, nose drops spray, suppository, or pessary.

19. The method of claim 18, wherein the pharmaceutical composition is administered parenterally, intramuscularly, subcutaneously, intravenously, intra-articularly, transdermally, orally, bucally, as a suppository or pessary, topically, or as an aerosol spray or drops.

20. The method of claim 19, wherein the composition is administered intravenously at a dose of about 0.1 to about 300 mg/kg/day.

21. The method of claim 19, wherein the pharmaceutical composition is applied topically as a liquid, ointment or cream, and the compound is present in an amount of from about 0.01 to about 100 mg/ml of the pharmaceutical composition.

22. The method of claim 12, wherein the compound is 4-hydroxy-2,2,6,6-tetramethylpiperidine-1-oxyl, and the anti-oxidative stress effective amount is from about 0.1 to about 300 mg/kg/day orally or by intravenous injection, or about 0.1 to about 200 mg/kg/day by inhalation.

23. A method of prolonging the storage life of human or animal cells, tissues, or organs in vitro, comprising contacting said cells, tissues, or organs in vitro with a solution containing an anti-oxidative stress effective amount of a compound selected from the group consisting of the oxidized form of a metal-independent nitroxide, the oxidized form of an oxazolidine compound capable of forming an oxazolidine-1-oxyl, and a physiologically acceptable salt thereof, to protect said cells, tissues, or organs from oxidative stress.

24. The method of claim 23, wherein said compound is 4-hydroxy-2,2,6,6-tetramethylpiperidine-1-oxyl.

25. A method of inducing weight reduction in humans or animals, comprising administering to a human or animal a composition containing a weight reduction effective amount of a compound selected from the group consisting of a metal-independent nitroxide, an oxazolidine compound capable of forming an oxazolidine-1-oxyl, and a physiologically acceptable salt thereof.

26. The method of claim 25, wherein said compound is 4-hydroxy-2,2,6,6-tetramethylpiperidine-1-oxyl.

27. A pharmaceutical composition, comprising an anti-oxidative stress effective amount of a compound selected from the group consisting of the oxidized form of a metal-independent nitroxide, the oxidized form of an oxazolidine compound capable of forming an oxazolidine-1-oxyl, and a physiologically acceptable salt thereof, and a biologically acceptable carrier, wherein the compound has the formula:

wherein $R_3$ is selected from the group consisting of –O. and —OH, and $R_4$ and $R_5$ combine together with the nitrogen to form a heterocyclic group, or wherein $R_4$ and $R_5$ themselves comprise a substituted or unsubstituted cyclic or heterocyclic group, or a physiologically acceptable salt thereof, said heterocyclic group being selected from the group consisting of a piperidine, pyrrole, imidazole, oxazole, thiazole, pyrazole, 3-pyrroline, pyrrolidine, pyridine, pyrimidine, purine, and a derivative thereof, and wherein said pharmaceutical composition is in a form selected from the group consisting of an emulsion, suspension, ointment, cream, aerosol, granule, powder, spray, tablet, capsule, sachet, lozenge, ampoule, pessary, and suppository.

28. The pharmaceutical composition of claim 27, wherein $R_4$ and $R_5$ combine together with the nitrogen to form a substituted or unsubstituted heterocyclic group.

29. The pharmaceutical composition of claim 28, where $R_4$ and $R_5$ combine together with the nitrogen atom to form a substituted or unsubstituted piperidine group.

30. The pharmaceutical composition of claim 29, wherein $R_4$ and $R_5$ combine together with the nitrogen atom to form a piperidine group having one or more methyl substituents and at least one hydroxy substituent.

31. The pharmaceutical composition of claim 30, wherein said piperidine ring is substituted at the 4-position with a hydroxy group and at the 2- and 6-positions with at least one methyl group.

32. The pharmaceutical composition of claim 27, wherein the carrier is an ointment or a cream.

33. The pharmaceutical composition of claim 27, wherein said pharmaceutical composition is a topical composition.

34. The pharmaceutical composition of claim 27, wherein the compound is 4-hydroxy-2,2,6,6-tetramethylpiperidine-1-oxyl, the compound is present in an amount of from about 0.01 to about 100 mg/ml of the total composition, and the carrier is an ointment or a cream.

* * * * *